United States Patent
Mizutani

(10) Patent No.: US 6,676,649 B2
(45) Date of Patent: *Jan. 13, 2004

(54) SANITARY NAPKIN HAVING UPPER AND LOWER ABSORBENT CORES

(75) Inventor: Satoshi Mizutani, Kagawa-ken (JP)

(73) Assignee: Uni-Charm Corporation, Ehime-ken (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/390,010

(22) Filed: Sep. 3, 1999

(65) Prior Publication Data

US 2002/0013562 A1 Jan. 31, 2002

(30) Foreign Application Priority Data

Sep. 8, 1998 (JP) .............................. 10-253634

(51) Int. Cl.⁷ ................................. A61F 13/15
(52) U.S. Cl. ............. 604/387; 604/385.03; 604/385.16
(58) Field of Search ...................... 604/385.101, 385.01, 604/378, 385.23, 385.22, 385.26, 385.03, 385.14, 385.16, 387

(56) References Cited

U.S. PATENT DOCUMENTS

| | | | | |
|---|---|---|---|---|
| 4,342,314 A | * | 8/1982 | Radel et al. ................. 128/287 |
| 5,324,278 A | * | 6/1994 | Visscher et al. .......... 604/385.1 |
| 5,545,156 A | * | 8/1996 | DiPalma et al. .......... 604/385.1 |
| H1634 H | * | 2/1997 | Oetjen et al. ............. 604/385.1 |
| 5,704,928 A | * | 1/1998 | Morita et al. ............. 604/385.1 |
| 5,853,403 A | * | 12/1998 | Tanzer et al. ............. 604/385.1 |
| 5,947,945 A | * | 9/1999 | Cree et al. ................... 604/368 |
| 6,042,575 A | * | 3/2000 | Osborn, III et al. ........ 604/387 |
| 6,102,892 A | * | 8/2000 | Putzer et al. ............... 604/101 |
| 6,296,628 B1 | * | 10/2001 | Mizutani .................... 604/387 |

FOREIGN PATENT DOCUMENTS

| | | |
|---|---|---|
| EP | 0 815 816 A1 | 1/1998 |
| EP | 0 908 162 A2 | 4/1999 |
| JP | 05115506 | 5/1993 |
| JP | U-7-33315 | 6/1995 |
| WO | WO 97/39710 | 10/1997 |
| WO | WO 98/58614 | 12/1998 |

OTHER PUBLICATIONS

Copy of European Search Report mailed Nov. 9, 2001.

* cited by examiner

Primary Examiner—Weilun Lo
Assistant Examiner—Michele Kidwell
(74) Attorney, Agent, or Firm—Butzel Long

(57) ABSTRACT

A sanitary napkin which includes a liquid-pervious topsheet, a liquid-impervious backsheet and a liquid-absorbent core disposed therebetween. The topsheet extends to transversely opposite side edges of the napkin with interposition of pleats, along which side edges the topsheet is bonded to the backsheet. The core includes a lower absorbent core and an upper absorbent core. The pleats lie between transversely opposite side edges of the lower absorbent core and transversely opposite side edges of the upper absorbent core. The topsheet are provided along the opposite side edge of the upper absorbent core with elasticity being effective longitudinally of the napkin.

6 Claims, 4 Drawing Sheets

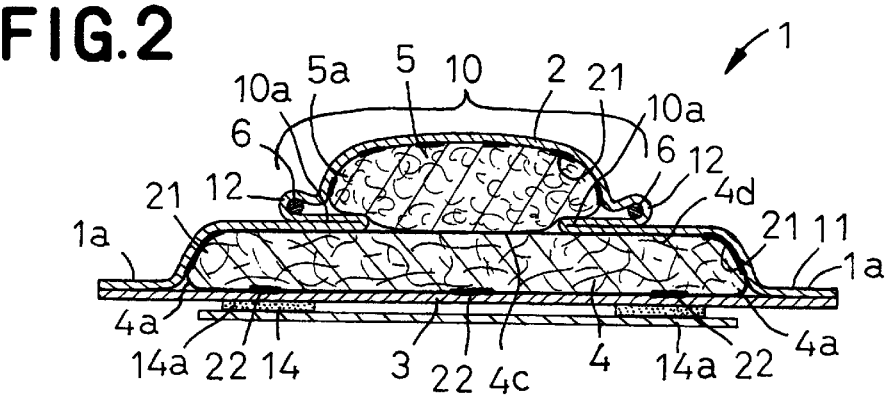
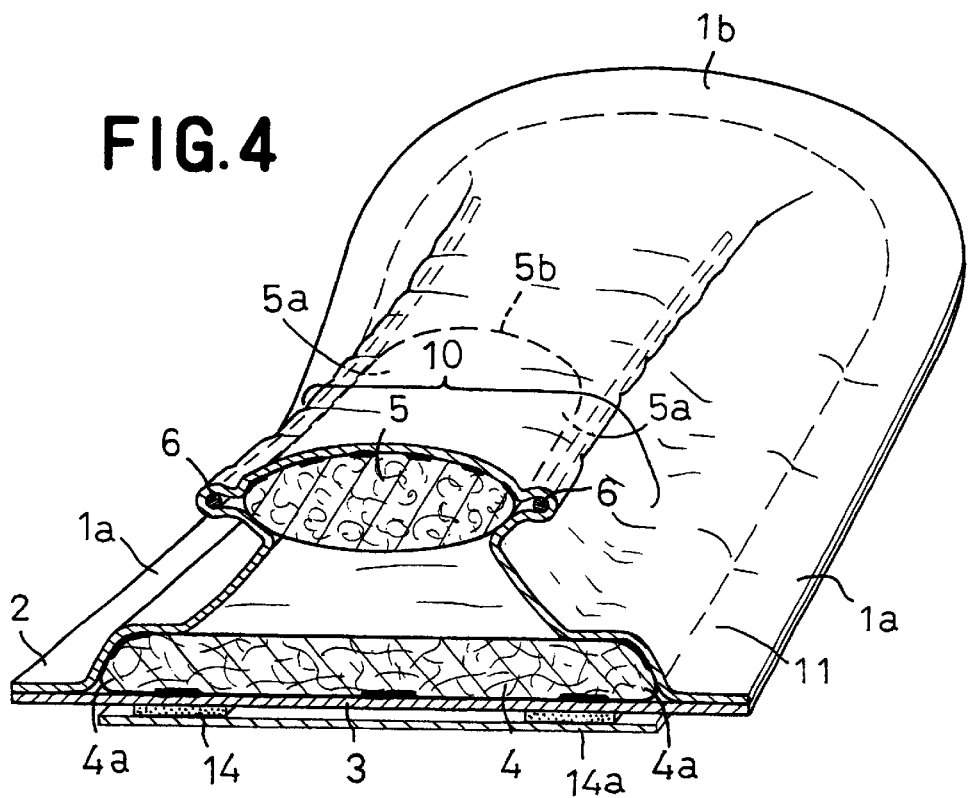

SANITARY NAPKIN HAVING UPPER AND LOWER ABSORBENT CORES

BACKGROUND OF THE INVENTION

This invention relates to a sanitary napkin absorption and containment of menstrual discharge.

Japanese Utility Model Application Disclosure Gazette (Kokai) No. Hei7-33315 discloses a sanitary napkin consisting of upper and lower napkins each comprising a liquid-absorbent core covered with a liquid-pervious sheet. The upper napkin having a longitudinal dimension smaller than that of the lower napkin lies on a middle region of the lower napkin. A pair of elastic members extend longitudinally along transversely opposite side edges of the upper napkin beyond longitudinally opposite ends of the upper napkin and are fixed under tension to longitudinally opposite ends of the lower napkin at respective ends of these elastic members. The upper and lower napkins can relatively move without being restricted by each other within a considerably wide range.

In the known sanitary napkin, a lower surface of the upper napkin normally remains in contact with the upper surface of the lower napkin and operate as if these two napkins are assembled in a single napkin. Specifically, the liquid-pervious sheet covering the upper napkin is placed upon the liquid-pervious sheet covering the lower napkin. Such situation may obstruct a rapid transfer of menstrual discharge from the upper napkin to the lower napkin. In consequence, there is apprehension that a portion of menstrual discharge might leak sideways before it transfers to the lower napkin especially when a large quantity of menstrual discharge is discharged.

SUMMARY OF THE INVENTION

It is an object of this invention to provide a sanitary napkin including upper and lower liquid-absorbent cores in which so that menstrual discharge can rapidly transfer from the upper absorbent core to the lower absorbent core and thereby any apprehensive leakage of menstrual discharge can be avoided.

According to the present invention, there is provided a sanitary napkin including a liquid-pervious topsheet, a liquid-impervious backsheet and a liquid-absorbent core disposed between the topsheet and the backsheet, the sanitary napkin being contoured by a pair of opposite side edges extending longitudinally of the napkin and a pair of opposite ends extending between the pair of opposite side edges, wherein: the topsheet is dimensioned to have a width larger than that of the backsheet and transversely opposite sides of the topsheet is folded back inwardly of the napkin along a pair of folding lines extending longitudinally of the napkin and the folded portions are further folded outwardly of the napkin so as to form a pair of pleats and extend from the pleats to the respective side edges of the napkin along which the topsheet is bonded to the backsheet; the absorbent core includes a lower absorbent core and an upper absorbent core, the lower absorbent core is placed on an inner surface of the backsheet and extends between the opposite side edges and between longitudinally opposite ends of the napkin; the upper absorbent core is dimensioned to be shorter than the lower absorbent core and separably placed upon an inner surface of the lower absorbent core; the upper absorbent core is bonded to an inner surface of the topsheet so that the upper absorbent core is spaced from the opposite ends of the napkin and the pleats lie between the transversely opposite side edges of the lower absorbent core and the transversely opposite side edges of the upper absorbent core; and at least portions of said topsheet are provided along the opposite side edges of the upper absorbent core with elasticity being effective longitudinally of the napkin.

According to one embodiment of this invention, the upper absorbent core lies to one of the longitudinally opposite ends of the napkin.

According to another embodiment of this invention, the elasticity of the topsheet is given by elastic members in the form of threads, ribbons or sheets.

According to still another embodiment of this invention, the elasticity of the topsheet is given by an elastic sheet used as the topsheet being bonded under tension in the longitudinal direction.

According to a further embodiment of this invention, the maximum dimension by which the upper absorbent core is spaced from the lower absorbent core in response to contraction of the topsheet is in a range of 5~50 mm.

According to an additional embodiment of this invention, a plurality of said pleats are formed on both sides of the upper absorbent core, respectively.

BRIEF DESCRIPTION OF THE DRAWINGS

FIG. 2 is a sectional view taken along a line A—A in FIG. 1;

FIG. 4 is a perspective view of the napkin inclusive of its section taken along a line B—B in FIG. 3.

DETAILED DESCRIPTION OF THE PREFERRED EMBODIMENT

Details of a sanitary napkin according to th present invention will be more fully understood from the description given hereunder with reference to the accompanying drawings.

Figure 1:
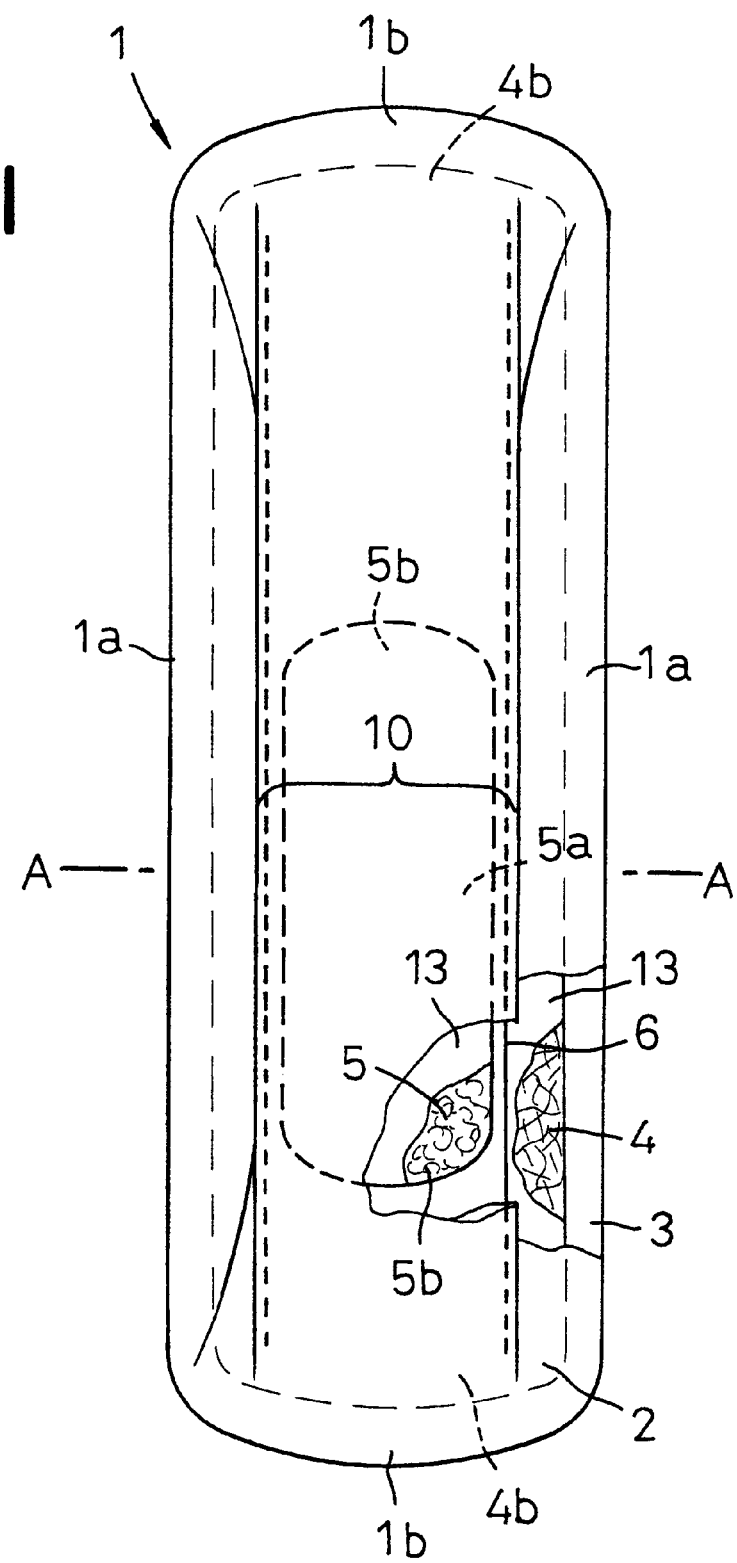
FIG. 1 is a plan view showing a partially cut away sanitary napkin according to the invention.

FIG. 1 is a perspective view showing a partially cut away sanitary napkin 1 and FIG. 2 is a sectional view taken along a line A—A in FIG. 1. A sanitary napkin 1 is elongate and comprises a liquid-pervious topsheet 2, a liquid-impervious backsheet 3, a liquid absorbent lower absorbent core 4 and a liquid absorbent upper absorbent core 5 overlying the lower absorbent core 4. The sanitary napkin 1 is contoured by a pair of transversely opposite side edges 1a extending longitudinally and a pair of longitudinally opposite ends 1b extending between the pair of side edges 1a.

In order to cover a portion 10 of the topsheet 2, a transversely middle region of the napkin 1 is folded back inwardly of the napkin 1 along a pair of folding lines 12 extending in parallel to the respective side edges 1a of the napkin 1. Then the portions folded in this manner are folded outwardly of the napkin 1 so as to form a pair of pleats 10a and thereafter extend to the respective side edges 1a of the napkin 1, along which the topsheet 2 is bonded to the backsheet 3. As will be understood from such manner in which the topsheet 2 covers the transversely middle region of the napkin 1, the topsheet 2 is dimensioned to have a width considerably larger than that of the backsheet 3.

The backsheet 3 is substantially flat and is formed on its lower surface with a pair of adhesive fastening zones 14 used to fasten the napkin 1 to an undergarment worn by a napkin wearer and protectively covered with respective release sheets 14a.

The lower absorbent core 4 is placed on an inner surface of the backsheet 3 and extends between the side edges 1a and between the longitudinally opposite ends 1b. An upper surface of the lower absorbent core 4 has its transversely middle region 4c placed in contact with a lower surface of the upper absorbent core 5. Transversely opposite side edges 4a of the lower absorbent core 4 are bonded to a lower surface of the topsheet 2 by means of adhesive agent 21. Intermediate regions 4d defined between the middle region 4c and the respective side edges 4a are not bonded to the topsheet 2. Both the middle region 4c and the intermediate regions 4d are not bonded to the upper absorbent core 5 as well as to the topsheet 2 so that the regions 4c, 4d can be freely spaced from the upper absorbent core 5 and the topsheet 2. The longitudinally opposite ends 4b of the lower core 4 are bonded to an inner surface of the topsheet 2 at locations slightly inside the longitudinally opposite ends 1b of the napkin 1. A lower surface of the lower absorbent core 4 is bonded to an inner surface of the backsheet 3 by means of adhesive agent 22.

The upper absorbent core 5 is smaller than the lower absorbent core 4 in length as well as in width. Preferably, the upper absorbent core 5 is formed so that its thickness gradually decreases from the middle region toward the side edges and is separably placed upon the inner surface of the lower absorbent core 4. Longitudinally opposite ends 5b of the upper absorbent core 5 lie inside the respective side edges 4b of the lower absorbent core 4 and are spaced from the respective ends 1b of the napkin 1 by a predetermined distance. Preferably, the upper absorbent core 5 lies to the front end of the napkin 1 during actual use of the napkin 1. The upper surface of the upper absorbent core 5 defined between its transversely opposite side edges 5a is bonded to the inner surface of the portion 10 of the topsheet 2 to cover the transversely middle region of the napkin 1 by means of adhesive agent 21.

Elastic members comprise ribbon-like elastic members or thread-like elastic members between the longitudinally opposite ends 1b of the napkin 1 and are secured under tension to the inner surface of the topsheet 2 along the side edges of the upper absorbent core 5 by means of adhesive agent (not shown). These elastic members 6 have a contractile force sufficient to longitudinally curve the napkin 1 convexly downward as the elastic members 6 contract. Elongation percentage of these elastic members 6 is 20~200%. It should be understood that the elastic members 6.

Portions of the topsheet 2 extending longitudinally along the respective elastic members 6 further extend outward beyond the side edges of the upper absorbent core 5. It is also possible to provide elastic member along respective free edges of these extension to thereby improve a side flap function of these extensions tending to rise toward the wearer's skin.

Portions of the topsheet 2 and the backsheet 3 extending outward beyond a peripheral edge of the lower absorbent core 4 and placed upon each other are bonded together by means of adhesive agent or heat-sealing treatment to define the transversely opposite side edges 1a and the longitudinally opposite ends 1b of the napkin 1. During actual use of the napkin 1, the lower surface of the upper core 5 is normally in contact with the upper surface of the lower absorbent core 4, the adhesive fastening zones 14 of the backsheet 3 are fastened to an inner surface of the undergarment worn by the napkin wearer, and the upper surface of the upper absorbent core 5 is placed against the wearer's pudendum with interposition of the topsheet 2. Menstrual discharge once absorbed by the upper absorbent core 5 transfers to the lower absorbent core 4 so far as the lower absorbent core 4 is maintained in contact with the upper absorbent core 5.

Figure 3:
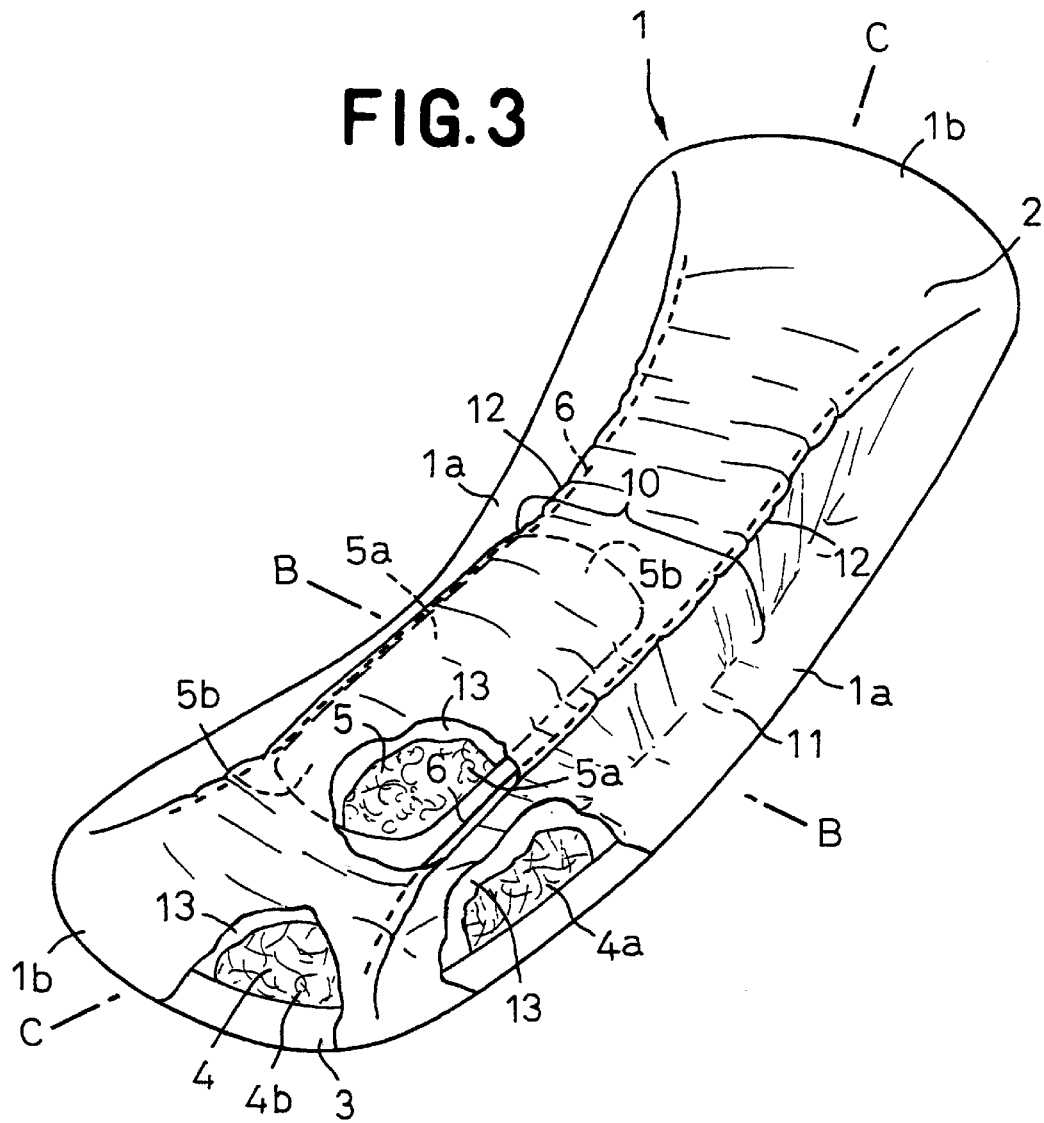
FIG. 3 is a perspective view showing the partially cut away napkin with its elastic members contracting.

FIG. 3 is a perspective view showing the partially cut away napkin 1 with the elastic members 6 contracting and FIG. 4 is a perspective view of the napkin 1 inclusive of a section taken along a line B—B in FIG. 3. Supposed that the napkin 1 is still not put on the wearer's body, the napkin 1 is longitudinally curved convexly downward as the elastic members 6 contract against a rigidity of the lower absorbent core 4 and, in consequence, the upper absorbent core 5 is spaced upward from the lower absorbent core 4. Thus, the pleats 10a of the topsheet 2 vertically spread between the upper absorbent core 5 and the lower absorbent core 4. Contraction of the elastic members 6 causes the topsheet 2 to be formed with gathers along its zones in which the elastic members 6 are bonded to the topsheet 2.

Figure 5:
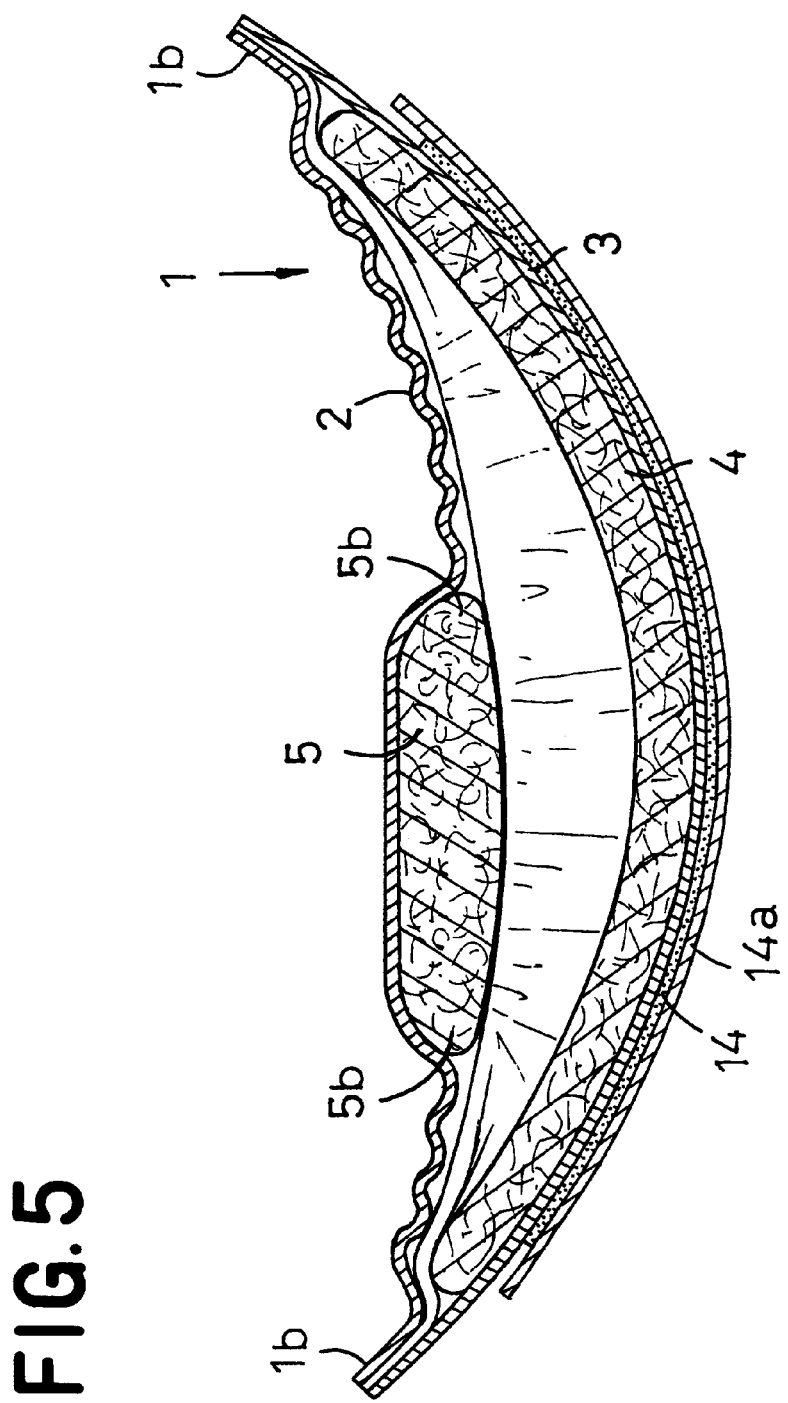
FIG. 5 is a sectional view taken along a line C—C in FIG. 3.

FIG. 5 is a sectional view taken along a line C—C in FIG. 3 as shown, the upper absorbent core 5 extends practically in a horizontal direction longitudinally of a napkin 1. The maximum dimension as measured from the upper surface of the lower absorbent core 4 to the lower surface of the upper absorbent core 5 is preferably in a range of 5~50 mm. Even if the undergarment slips down and the napkin 1 is moved away from the wearer's body, the upper absorbent core 5 is spaced from the lower absorbent core 4 to remain in contact with the wearer's pudendum so that menstrual discharge may be rapidly absorbed. In this manner, the napkin 1 is free from any apprehension that undesirable leakage of menstrual discharge might readily occur.

In aa illustrative embodiment of the napkin 1 according to the present, both the upper absorbent core 5 and the lower absorbent core 4 are formed by compressing fluff pulp or a mixture of fluff pulp and superabsorptive polymer particles and covering it with a water-absorbent sheet 13 such as tissue paper.

The elastic member 6 may be made of synthetic rubber, natural rubber, a composite material such as a film combined with synthetic rubber, a spun bond nonwoven fabric or a melt blown nonwoven fabric both comprising synthetic rubber as its principal component or a nonwoven fabric to which a suitable elastic material is secured under tension, or the like. In the case of the elastic member 6 comprising a nonwoven fabric, this nonwoven fabric is secured under tension to the inner surface of the topsheet 2 between the longitudinally opposite ends 5b of the upper absorbent core 5 and the longitudinally opposite ends 1b of the napkin 1. While the elastic members 6 are shown to extend between the longitudinally opposite ends 1b, it is also possible to arrange so that these elastic members 6 extend only between the longitudinally opposite ends 5b of the upper absorbent core 5 and the longitudinally opposite ends 1b of the napkin 1, respectively.

Stock material useful for the topsheet 2 includes a hydrophobic nonwoven fabric, a hydrophobic nonwoven fabric treated with hydrophiling agent or a hydrophile nonwoven fabric made of fibers mixed with hydrophiling agent. A water-pervious sheet having an elasticity also can be used as stock material for the topsheet 2. In this case, such elastic sheet may be secured, under tension between the longitudinally opposite ends 1b of the napkin 1, to the portions of the backsheet 3 extending outward beyond the peripheral edge of the lower absorbent core 4. In this manner, use of the elastic members 6 can be eliminated. It is also possible to use a liquid-pervious apertured film of thermoplastic synthetic resin in the place of the nonwoven fabric and such film includes an elastic film. No matter what type of stock material is used, the topsheet 2 may be formed particularly in its region covering the upper absorbent core 5 with a plurality of liquid-pervious apertures.

With the sanitary napkin according to this invention, undesirable leakage of menstrual discharge can be effectively avoided even when the undergarment worn by the napkin wearer slips down and consequently the napkin adhesively fastened to the inner surface of the undergarment crotch region moves away from the wearer's body, because the upper absorbent core is spaced upward from the lower absorbent core so as to remain in contact with the wearer's body. The upper absorbent core is free to move relatively to the lower absorbent core in a sufficiently wide range to ensure that the upper absorbent core can remain in contact with the wearer's body and thereby avoid undesirable leakage of menstrual discharge even when the lower absorbent core moves together with the undergarment back and forth or rightward and leftward relative to the wearer's body.

In the normal state of this napkin, the upper and lower absorbent cores are in direct contact with each other so that transfer of menstrual discharge from the upper absorbent core to the lower absorbent core can rapidly occur.

What is claimed is:

1. A sanitary napkin comprising:

a liquid-pervious topsheet;

a liquid-impervious backsheet; and a lower and an upper liquid-absorbent core each disposed between the topsbeet and the backsheet, said sanitary napkin being contoured byapair of opposite side edges extending longitudinally of said napkin and a pair of opposite ends extending between said pair of opposite side edges, said topaheet being dimensioned so as to have a width that is larger than a width of said backsheet, opposite side portions of said topsheet being folded back inwardly along longitudinally extending fold lines to form folded portions, said folded portions being further folded outwardly so as to form a pair of pleats, said opposite side portions further extending outwardly from said pair of pleats to the respective side edges of said napkin along which said topsheet is bonded to said backsheet, said lower absorbent core being placed on an inner surface of said backsheet and extending between said opposite side edges and between said opposite ends of said napkin, said upper absorbent core being longitudinally and laterally shorter than said lower absorbent core, said upper absorbent core being bonded to an inner surfacc of said topaheet so that said upper absorbent core is spaced apart from the opposite ends of said napkin and said pair of pleats lie between transversely opposite side edges of said lower absorbent core and transversely opposite side edges of said upper absorbent core, and at least portions of said topsheet provided along said opposite side edges of said upper absorbent core are resiliently stretchable longitudinally and produce an elastic pulling force that pulls the upper absorbent core upward and thereby causes the upper absorbent core to separate and be spaced apart from the lower absorbent core.

2. A sanitary napkin according to claim 1, wherein said upper absorbent core is longitudinally off-center of said napkin.

3. A sanitary napkin according to claim 1, wherein the portions of said topsheet that are resiliently stretchable longitudinally comprise elastic members.

4. A sanitary napkin according to claim 1, wherein said topsheet comprises an elastic sheet.

5. A sanitary napkin according to claim 1, wherein a maximum distance by which said upper absorbent core can be spaced apart from said lower absorbent core in response to contraction of said topsheet is in a range of about 5 mm to about 50 mm.

6. A sanitary napkin according to claim 1, wherein a plurality of said pleats are formed on both sides of said upper absorbent core, respectively.

* * * * *